United States Patent [19]

Himmele et al.

[11] 3,975,400

[45] Aug. 17, 1976

[54] METHOD OF CONTINUOUSLY PRODUCING γ-BUTYROLACTAMS

[75] Inventors: Walter Himmele, Walldorf; Ernst Hofmann, Ludwigshafen; Herwig Hoffmann, Frankenthal; Reinhold Plass, Ludwigshafen, all of Germany

[73] Assignee: Badische Anilin- & Soda-Fabrik Aktiengesellschaft, Ludwigshafen (Rhine), Germany

[22] Filed: Feb. 21, 1973

[21] Appl. No.: 334,398

Related U.S. Application Data

[63] Continuation of Ser. No. 71,738, Sept. 14, 1970, abandoned.

[30] Foreign Application Priority Data

July 27, 1968 Germany............................ 1795007

[52] U.S. Cl. ..................................... 260/326.5 FN
[51] Int. Cl.² ..................................... C07D 207/26
[58] Field of Search........................... 260/326.5 FN

[56] References Cited
UNITED STATES PATENTS 3,133,085 5/1964 Start ................................ 260/326.5

FOREIGN PATENTS OR APPLICATIONS 935,544 11/1955 Germany ......................... 260/239.3

OTHER PUBLICATIONS

Sidel'Kovskaya, et al. *Chemical Abstracts* vol. 59: 5110f (1963).
Moore, et al., "Physical Chemistry, 1962, p. 177–178.

*Primary Examiner*—Donald G. Daus
*Assistant Examiner*—Mark L. Berch
*Attorney, Agent, or Firm*—Johnston, Keil, Thompson & Shurtleff

[57] ABSTRACT

Method of producing γ-butyrolactams by reacting γ-butyrolactones with ammonia in the presence or absence of water at elevated temperatures and pressures. The reaction is carried out continuously at temperatures ranging from 180° to 340°C whilst maintaining pressures which are at least 10 percent higher than the pressure equal to the sum of the partial pressures of the reactants at the temperature used. γ-Butyrolactams are valuable intermediates, for example in the manufacture of polymers, pharmaceuticals and solvents.

4 Claims, 1 Drawing Figure

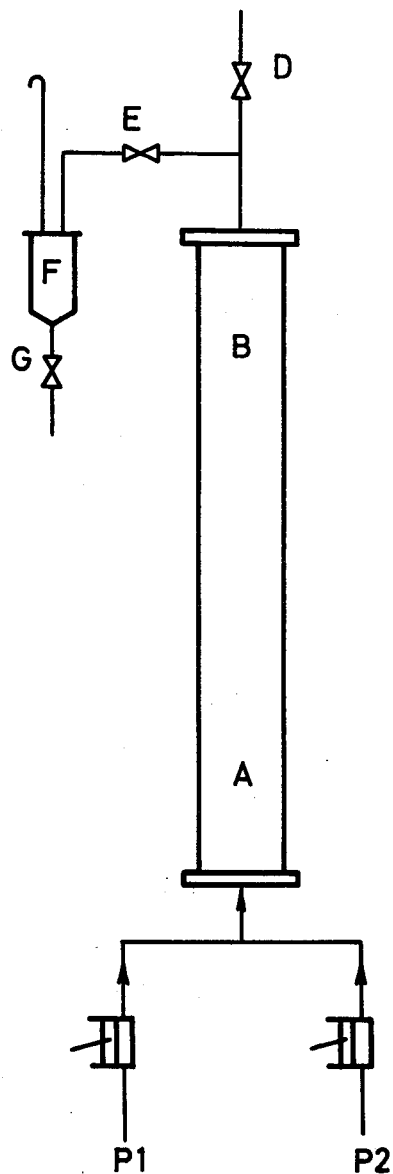

METHOD OF CONTINUOUSLY PRODUCING γ-BUTYROLACTAMS

This is a continuation of application Ser. No. 71,738, filed Sept. 14, 1970, now abandoned.

The present invention relates to a method of producing γ-butyrolactams by reacting γ-butyrolactones with ammonia.

German Pat. No. 935,544 reveals a method of producing pyrrolidone-2 by reacting γ-butyrolactone with concentrated ammonia at an elevated temperature and the autogenic pressure of the reactants in the autoclave. The yields obtained by this method are, however, not satisfactory for industrial use of the method. Furthermore, the method produces undesirable by-products.

We have now found that γ-butyrolactams may be advantageously produced by reacting γ-butyrolactones with ammonia, in the presence or absence of water, at an elevated temperature and pressure, provided that the reaction is carried out at temperatures ranging from 180° to 340°C whilst maintaining pressures which are at least 10 percent higher than the pressure resulting as the sum of the partial pressures of the reactants at the temperature at which the reaction is carried out.

The novel method produces γ-butyrolactams of good quality in yields of more than 95 percent. Furthermore, in the method of the invention conversions of the γ-butyrolactones of virtually 100 percent are obtained and the separation of starting materials from the resulting lactams is thus not necessary.

Suitable starting materials for the method of the invention are γ-butyrolactone itself and γ-butyrolactones carrying inert substituents such as alkyl groups or alkoxy groups of from 1 to 4 carbon atoms. As examples there may be mentioned 3-ethyl-γ-butyrolactone and 4-methyl-γ-butyrolactone. The concentration of the ammonia used in the method of the invention may be varied within wide limits. In general, the ammonia is used in a concentration of from 15 to 100 percent by weight, preferably from 50 to 100 percent by weight of the total weight of pure ammonia and any water present.

An important feature of the method of the invention is that the pressure in the reaction chamber must be at least 10 percent and preferably at least 20 percent higher than the pressure resulting as the sum of the partial pressures of the reactants at the temperature at which the reaction is carried out. If the reaction is carried out at the autogenic pressure of the reaction system, markedly poorer yields are achieved and the formation of undesirable by-products, some of which are basic in nature, is observed. The upper limit of the pressure at which the reaction is carried out is generally taken as 250 percent, preferably 150 percent, above the autogenic pressure of the reaction system. The use of even higher pressures will lead to slight improvements in yield, which are offset, however, by the need to use expensive pressure apparatus. In general, the reaction pressures range from 25 to 280, preferably from 45 to 130, atmospheres.

The temperatures at which the reaction is carried out range from 180° to 340°C and preferably from 190° to 290°C. The average residence times of the reaction mixture in the reaction zone are generally from 10 minutes to 28 hours, preferably from 45 to 180 minutes. The continuous process may be carried out, for example, by pressure-feeding the starting lactone, optionally in admixture with water, and the ammonia to the bottom of a heated vertical high-pressure tube. The reaction pressure may be simply controlled by means of a relief valve which may be conveniently positioned at the discharge end of the high-pressure tube.

The reaction mixture is worked up in the usual manner, for example by driving off the excess ammonia and fractionally distilling the residue. The recovered ammonia may be recycled to the reaction.

γ-Butyrolactams are valuable intermediates, for example in the manufacture of polymers and pharmaceuticals. They are also used as solvents.

The method of the invention is further illustrated in the following Examples, in which the parts are by weight.

EXAMPLE 1 a. Into an electrically heated vertical high-pressure tube of 800 cm length (see accompanying drawing) and equipped at its top end with a relief valve D controlled via pressure regulators there is pumped a mixture of starting lactone and water by feed pump P1 and non-aqueous ammonia by feed pump P2 such that these liquids pass into the entry zone A. The temperature in the entry zone A is adjusted to 270°C. Due to the fact that the relief valve D is positioned above the exit zone B it is a simple matter to maintain the whole system filled with liquid. Any gas phase which may form will naturally travel to the top of the system quicker than the liquid and will be preferentially released. For control purposes there is provided a small trap F below the relief valve D, which trap makes it possible to determine, by means of a special take-off devices (valves E and G), whether a gas phase has formed below the relief valve D or not. All tests are carried out in such a manner that the reaction chamber is virtually completely filled with the liquid reaction mixture. After removal of the reaction product from the reaction tube, the excess ammonia is evaporated off and the water is removed from the crude product by distillation. The residue is then fractionally distilled under reduced pressure. The quality of the resulting lactam is determined by gas chromatography. The major portion of the by-products remains in the distillation residue which, in the case of the production of pyrrolidone-2, mainly consists of γ-(N-pyrrolidonyl)-butyramide and the corresponding nitrile. The autogenic pressure of the reaction system is determined by noting the pressure at which the gas phase in the reaction tube just disappears.

b. Using the apparatus described under (a) above, 1,000 parts of γ-butyrolactone, 500 parts of water and 1,100 parts of non-aqueous ammonia are pumped into the tube per hour. The gas phase in the reaction tube disappears at a pressure of 57 atmospheres at 270°C. Reactions in accordance with the present invention are carried out at 80, 100, 130 and 200 atmospheres. For purposes of comparison, a reaction is also carried out at 60 atmospheres. After each adjustment, steady-state conditions are achieved after about 24 hours. 12 Hours later, samples are taken, worked up as described under (a) above and examined. The test results are given in the following Table 1.

Table 1

| Pressure (atm.) | Distillation residue in % by weight of dehydrated crude product | Butyrolactone in distillate (% by wt.) | Yield of pyrrolidone on butyrolactone (% of theory) |
| --- | --- | --- | --- |
| 80 | 8.0 | 0.18 | 91.1 |
| 100 | 7.0 | 0.14 | 92.7 |
| 130 | 5.7 | 0.07 | 94.3 |
| 200 | 4.3 | 0.05 | 95.2 |
| 60 | 11.8 | 0.78 | 87.2 |

EXAMPLE 2

The procedure described in Example 1 is followed for the reaction of 670 parts/hr of butyrolactone, 330 parts/hr of water and 700 parts/hr of non-aqueous ammonia at 270°C. The gas phase in the reaction tube disappears at a pressure of 54 atmospheres at 270°C. Reactions in accordance with the present invention are carried out at pressures of 100, 150 and 200 atmospheres. A comparative test is carried out at 58 atmospheres. The test results are given in Table 2.

Table 2

| Pressure (atm.) | Distillation residue in % by weight of dehydrated crude product | Butyrolactone in distillate (% by wt.) | Yield of pyrrolidone based on butyrolactone (% of theory) |
| --- | --- | --- | --- |
| 100 | 6.7 | 0.14 | 92.5 |
| 150 | 5.4 | 0.05 | 94.4 |
| 200 | 3.4 | 0.02 | 96.1 |
| 58 | 12.4 | 0.77 | 87.0 |

EXAMPLE 3

The procedure described in Example 1 is followed for the reaction of 1,500 parts/hr of butyrolactone, 1,500 parts/hr of water and 1,600 parts/hr of non-aqueous ammonia at 270°C. The gas phase in the reaction tube disappears at a pressure of 51 atmospheres at 270°C. Reactions in accordance with the present invention are carried out at pressures of 70, 85, 100 and 120 atmospheres. The results of the test are given in Table 3.

Table 3

| Pressure (atm.) | Distillation residue in % by weight of dehydrated crude product | Butyrolactone in distillate (% by wt.) | Yield of pyrrolidone based on butyrolactone (% of theory) |
| --- | --- | --- | --- |
| 70 | 7.8 | 0.29 | 91.0 |
| 85 | 6.7 | 0.23 | 92.6 |
| 100 | 5.8 | 0.17 | 93.9 |
| 120 | 4.9 | 0.09 | 95.0 |
| 55 | 12.9 | 0.79 | 85.5 |

We claim:

1. A liquid-phase process for continuously producing γ-butyrolactams which comprises passing a γ-butyrolactone selected from the group consisting of γ-butyrolactone and γ-butyrolactone having an alkyl or alkoxy group with 1 to 4 carbon atoms in said group as a substituent and liquid ammonia separately to the bottom of a vertical reaction tube, said reaction tube having a relief valve at its discharge and, maintaining the reaction mixture at a temperature of from 180° to 340°C and maintaining the pressure within said tube by means of said relief valve at a value which is from 10 to 250 percent higher than the sum of the partial pressures of the reactants at said temperature, said reaction tube being filled with liquid reaction mixture during said reaction any gas phase that is formed in said tube being released.

2. A process as set forth in claim 1 wherein said pressure is from 20 to 150 percent higher than the sum of the partial pressures of the reactants at said temperature.

3. A process as set forth in claim 1 wherein said γ-butyrolactone is γ-butyrolactone itself.

4. A process as set forth in claim 1 wherein the average residence time of the reaction mixture in said reaction tube is about 10 minutes to 28 hours.

* * * * *